(12) United States Patent
Chenik et al.

(10) Patent No.: US 8,551,500 B2
(45) Date of Patent: Oct. 8, 2013

(54) COMPOSITION COMPRISING THE N-TERMINAL REGION OF HISTONE H2B OF LEISHMANIA—USE THEREOF FOR INDUCING AN IMMUNE RESPONSE

(75) Inventors: Mehdi Chenik, La Marsa (TN); Hechmi Louzir, La Marsa (TN); Koussay Dellagi, Tunis-Babsaadoun (TN)

(73) Assignees: Institut Pastuer, Paris (FR); Institut Pasteur De Tunis, Tunis Belvedere (TN)

( * ) Notice: Subject to any disclaimer, the term of this patent is extended or adjusted under 35 U.S.C. 154(b) by 1158 days.

(21) Appl. No.: 12/149,841

(22) Filed: May 8, 2008

(65) Prior Publication Data

US 2010/0119532 A1    May 13, 2010

Related U.S. Application Data

(63) Continuation of application No. 11/898,879, filed on Sep. 17, 2007, now abandoned, which is a continuation of application No. PCT/FR2006/000597, filed on Mar. 17, 2006.

(30) Foreign Application Priority Data

Mar. 18, 2005  (FR) ...................... 05 02725

(51) Int. Cl.
*A61K 39/00* (2006.01)
*A61K 39/38* (2006.01)
*A61K 39/002* (2006.01)

(52) U.S. Cl.
USPC ............. 424/269.1; 424/184.1; 424/185.1; 424/265.1

(58) Field of Classification Search
None
See application file for complete search history.

(56) References Cited

U.S. PATENT DOCUMENTS

2002/0081320 A1 * 6/2002 Reed et al. ............. 424/269.1

FOREIGN PATENT DOCUMENTS

WO    WO 2005/044301    *    5/2005

OTHER PUBLICATIONS

Harlow et al (Antibodies A Laboratory Manual, 1988 Chapter 5, p. 72-74).*
Ellis, R.W. (Chapter 29 of "Vaccines" [Plotkin, S.A. et al. (eds) published by W. B. Saunders company (Philadelphia) in 1988.*
Chenik et al. Vaccine 24 (2006) 2521-2529, published online Dec. 28, 2005.*
Soto et al. Clin Exp Immunol, 1999, 115-342-349.*
Uniprot accession # Q9BJC7 Jun. 1, 2001.*

* cited by examiner

*Primary Examiner* — Oluwatosin Ogunbiyi
(74) *Attorney, Agent, or Firm* — Finnegan, Henderson, Farabow, Garrett & Dunner LLP (57) ABSTRACT

The invention concerns an immunogenic composition comprising: i) an antigenic polypeptide consisting of a fragment of the protein histone H2B of *Leishmania*, said fragment including the N-terminal region of said protein histone H2B, and ii) an adjuvant stimulating the immune response.

21 Claims, 7 Drawing Sheets

```
  M   A   S   S   R   S   A   S   R   K   A   S   N   P   K   S   H        18
 ATG GCC TCT TCT CGC TCT GCT TCC CGC AAG GCT TCC AAC CCG CAC AAG TCG CAC     54
     H2B1 P-Nd

R   K   P   K   R   S   N   W   V   Y   V   G   R   S   L   K   A   I     36
 CGC AAG CCG AAG CGC TCG TGG AAC GTG TAC GTG GGC CGC TCG CTG AAG GCG ATC    108

N   A   Q   M   S   M   S   H   R   T   M   K   I   V   N   S   Y   V     54
 AAC GCC CAG ATG TCG ATG TCG CAC CGC ACG ATG AAG ATC GTG AAC TCG TAC GTG    162
             H2B2 X-S                   H3B P-Nd

N   D   V   M   E   R   I   C   T   E   A   A   S   I   V   R   A   N     72
 AAC GAC GTG ATG GAG CGC ATC TGC ACC GAG GCC GCG TCG ATT GTT CGC GCG AAC    216

K   K   R   T   L   G   A   R   N   V   Q   T   A   V   R   I   V   L     90
 AAG AAG CGC ACG TTG GGT GCG CGC GAG GTG CAG ACG GCG GTG CGC ATT GTG CTG    270

P   A   E   L   A   K   H   A   M   A   E   G   T   K   A   V   S   S    108
 CCG GCG GAG CTC GCG AAG CAC GCC ATG GCT GAG GGC ACG AAG GCC GTG TCG AGC    324

A   S   A   *                                                            112
 GCG TCG GCT TGA                                                            336
   H3B P-Xh
```

COMPOSITION COMPRISING THE N-TERMINAL REGION OF HISTONE H2B OF LEISHMANIA—USE THEREOF FOR INDUCING AN IMMUNE RESPONSE

This is a continuation of application Ser. No. 11/898,879, filed Sep. 17, 2007, now abandoned, which is a continuation application of PCT International Application No. PCT/FR2006/000597, filed Mar. 17, 2006, which claimed priority of France Patent Application No. 0 502 725, filed Mar. 18, 2005, all of which are relied upon and incorporated herein by reference.

The present invention concerns an immunogenic composition comprising: i) an antigenic polypeptide consisting of a fragment of the H2B histone protein of *Leishmania*, said fragment including all or part of the N-terminal region of said H2B histone protein, and ii) an adjuvant stimulating the immune response.

The present invention also concerns a polypeptide consisting in a fragment of the H2B histone protein of *Leishmania*, said fragment comprising all or part of the N-terminal region of said H2B histone protein, a variant polypeptide retaining at least 50% identity, preferably at least 80% identity with said polypeptide, and a nucleic acid molecule coding for the polypeptide or the variant polypeptide.

The invention also concerns a vaccine with which protection may be obtained against an infection by *Leishmania*, the active ingredient of which comprises the polypeptide, the variant polypeptide or the nucleic acid molecule according to the present application, and an expression vector capable of expressing the polypeptide or the variant polypeptide, comprising the nucleic acid molecule.

Leishmaniases form a heterogeneous group of pathologies which affect several millions of individuals and are due to the infection of the animal or human host by a protozoan parasite of the genus *Leishmania* (Desjeux et al., 1996). The clinical expression of the infection is characterized by large polymorphism including an asymptomatic infection, simple or recurrent cutaneous forms, diffuse or anergic cutaneous forms, cutaneo-mucosal forms and deadly visceral forms in the absence of a specific treatment (WHO Expert Committee, 1990). During its cycle, the parasite alternates between two stages: the flagellated promastigote stage which is found in the digestive tract of the vector insect and the amastigote stage in the macrophage of the mammal host.

The design of an anti-leishmanian vaccine may be contemplated because it was clearly demonstrated in humans, that infection by *Leishmania* gives protective immunity to re-infection (Guirges et al., 1971; Davies et al., 1995). This protection is associated with the development of a cellular immune response specific to the parasite.

Several vaccine candidates were evaluated against infection by the *Leishmania* parasite, both in the murine model and in humans.

Presently, no vaccine for human or veterinary use has shown any significant effectiveness in protection against leishmaniases (Sharifi et al., 1998; Khalil et al., 2000; De Luca et al., 2001; Armijos et al., 2004).

These vaccines may be distinguished in three groups: first generation vaccines consist of promastigotes killed by heat or by irradiation; in spite of their innocuity, the efficiency of these vaccines has not yet been proved (Sharifi et al., 1998; Khalil et al., 2000; De Luca et al., 2001; Armijos et al., 2004).

Second generation vaccines consist of native proteins obtained by biochemical purification of recombinant proteins and synthetic peptides obtained by genetic engineering. Several proteins have been described in the literature as inducing significant protection in the experimental murine model. The most important ones are represented by the polyprotein Leish-111f composed of 3 strongly immunogenic proteins placed in tandem, the LeIF (*Leishmania* elongation Initiation Factor), the protein LmSTI1 (*L. major* STress-Inducible protein) and the protein TSA (Thiol-Specific Antioxidant). Several studies were able to shown that each of these proteins tested individually or associated with IL-12 is capable of inducing a very significant slowing down of the development of the disease in BALB/c mice infected with *L. major* (Skeiky et al., 1998; Coler et al., 2002; Skeiky et al., 2002; Campos-Neto et al., 2002). The LACK protein (leishmanial homolog of receptor for activated c kinase) in the presence of IL-12 is also capable of imparting protection to BALB/c mice against a virulent challenge by *L. major* (Gurunathan et al., 1997). Finally, the PSA-2 antigen purified from *Leishmania* imparts good protection to mice (Handman, 1995).

Third generation vaccines comprise DNA-based vaccines containing one or more genes coding for leishmanian antigens (Ibora et al., 2003; Campbell et al., 2003; Ramiro et al., 2003; Dumonteil et al., 2003).

Third generation vaccines also comprise leishmanias, the pathogenic power of which has been genetically attenuated by deleting virulent genes. The case of leishmanias deleted of the gene coding for dihydrofolate reductase thymidilate synthetase (dhfr-ts$^-$). Several studies have shown in the murine model that vaccination of mice with these dhfr-ts$^-$ parasites may induce partial protection against infection by *Leishmania* (Brodskyn et al., 2000; Streit et al., 2001). It is also possible to include in the third generation vaccines, vaccines based on synthetic peptides. Several vaccination tests were conducted with different peptides generally including T epitopes. The most known example is that of the PT3 peptide which corresponds to the "histidine zinc binding region" of gp63. Thus, this peptide in the presence of a "poloxamer 407" adjuvant is capable of imparting durable protection to sensitive BALB/c mice, following a challenge by *L. major* (Spitzer et al., 1999).

Certain authors were interested in histone proteins: the first work was conducted in 1999, in which Soto et al. (1999) showed that the H2B protein may be a target of the antibody response during canine leishmaniasis. Later on, Maalej et al. evaluated the H2B protein, as compared with other parasitic proteins, proposing it as an antigen for serological diagnosis of human visceral leishmaniasis, and showed that it may be an interesting target (Maalej et al., 2003).

As regards the cellular response, Probst et al. (2001) showed that the H2B protein in its recombinant form was capable of inducing strong proliferation of peripheral blood mononuclear cells (PBMC) in patients having being cured from skin leishmaniasis, caused by *L. major*. This proliferation was accompanied by a significant production of IFN-γ in the absence of IL-4 (Probst et al., 2001).

In the murine model of visceral leishmaniasis (VL) caused by *L. donovani*, Melby et al. (2000) showed that vaccination of sensitive BALB/c mice with a fraction of DNA vaccines obtained from a cDNA bank, notably containing H2B, was capable of partially protecting these mice after virulent challenge by *L. donovani*.

Very recently in the experimental leishmaniasis model with infection of BALB/c mice by *L. major*, Iborra et al., (2004) showed that vaccination of mice with a cocktail of DNA vaccine coding for histone proteins (H2A, H2B, H3 and H4) induced a significant immune response of the Th1 type with secretion of INFγ associated with partial protection of vaccinated mice subsequent to a challenge by *L. major*.

Moreover, it was demonstrated that the *Leishmania* parasite is capable of inducing activation of regulatory T cells (Belkaid et al., 2002), which will suppress the effector immune responses and allow multiplication and persistence of the parasite.

Corroborating data suggest that regulatory T cells are positively selected after strong interaction with peptides of the self (TCR-CMH-peptide) (Gavin and Rudensky, 2003).

The inventors were interested in the H2N histone protein as a vaccine candidate. More specifically, first of all, they put forward the hypothesis that certain preserved regions of the parasitic proteins may preferentially activate the regulatory cells whereas the divergent sequences would activate the effector cells, and also that a same parasite protein may contain peptides inducing regulatory responses and other inducers of effector responses.

The inventors comparatively analyzed the immunogenicity and protective role of both divergent amino-terminal and preserved carboxy-terminal regions of the recombinant H2B protein of *L. major* as well as of the entire protein.

They noticed that surprisingly, the amino-terminal (divergent) portion of H2B, adjuvated with CpG, imparts best protection to sensitive BALB/c mice against a virulent challenge by *L. major*. This truncated protein may be a good vaccine candidate against leishmaniases.

The invention relates to an immunogenic composition characterized in that it comprises: i) an antigenic polypeptide consisting in a fragment of the H2B histone protein of *Leishmania*, said fragment comprising all or part of the N-terminal region of said H2B histone protein, and ii) an adjuvant stimulating the immune response.

In a particular embodiment of the invention, the immunogenic active ingredient of said immunogenic composition consists in said antigenic polypeptide consisting in a fragment derived from the sole N-terminal portion of the H2B histone protein of *Leishmania*.

The term "fragment" applied to a polypeptide or more particularly to an antigen, is aimed at a portion of the relevant native protein, excluding the whole of said protein.

The N-terminal portion of a native polypeptide, for example of the H2B histone protein of *Leishmania*, generally represents less than half of the total sequence of amino acids of this polypeptide, the retained sequence being that of the N-terminal end.

In a specific example, the polypeptide according to the invention has a polypeptide sequence of less than 65 amino acids, preferably less than 50 amino acids. The polypeptide in this context has a sequence comprising at least 6 consecutive amino acids of the N-terminal portion of the relevant H2B antigen.

In a specific example, the length of the sequence of said polypeptide accounts for 10 to 45% of the length of the histone protein.

The amino acid sequence of a polypeptide according to the invention is for example the following: M A S S R S A S R K A S N P H K S H R K P K R S W N V Y V G R S L K A I N A Q M S M S H R T (residues 1-46 of SEQ ID NO: 1).

In a specific example, the polypeptide is characteristic of the H2B histone of *Leishmania major*.

The polypeptide may also be characteristic of the H2B histone protein of *L. Infantum, L. Donovani, L. Tropica, L. Enrietti*.

The sequences of the H2B histone proteins of these parasites have been described: H2B from *L. Infantum* was described in Soto M. et al., 1999; Antigenicity of the *Leishmania Infantum* histones H2B and H4 during canine viscerocutaneous leishmaniasis; Journal Clin. Exp. Immunol. 115 (2), 342-349 (1999); H2B from *L. Enrietti* was described in Genske J. E. et al., 1991; Structure and regulation of histone H2B mRNAs from *Leishmania Enrietti*; Mol. Cell. Biol. 11(1), 240-249 (1991).

The H2B protein sequences of *L. Donovani* and *L. Tropica* have not yet been described. However, the expected preservation at the H2B histone proteins of *Leishmania*, should be larger than 80%.

Generally, the polypeptide may be characteristic of a species selected from the whole of the *Leishmania* genus.

In a specific example, the polypeptide comprised in the immunogenic composition according to the invention is a purified polypeptide or a polypeptide isolated from its production environment.

In a specific example, said immunogenic composition comprises a DNA as a polynucleotide sequence coding for the polypeptide according to the invention. For example, the polynucleotide is inserted into an eukaryotic expression plasmid.

One or more amino acids of the polypeptide determined from an H2B histone protein of a *Leishmania* species, as illustrated above and designated by the expression "reference polypeptide", may be substituted, deleted or added in order to form a variant polypeptide retaining at least 50% identity, preferably at least 80% identity, with the reference polypeptide, said variant polypeptide retaining the immunogenic properties of the reference polypeptide.

The identity percentage between the reference polypeptide and the variant polypeptide is determined after having achieved optimum global alignment. This alignment may notably be obtained by using the "Needleman-Wunsch" (Needleman and Wunsch, 1970, J. Mol. Biol. 48:443-453) or the ClustalW algorithm (Higgins & Sharp, a package for performing multiple sequence alignment on a microcomputer, 1988, Dec. 15; 73(1): 237-44).

The notion of identity means that an amino acid at a determined position in the reference polypeptide is identical with a corresponding amino acid in the variant polypeptide which has been subject to alignment relatively to the reference polypeptide.

The fact that the sequence of the reference polypeptide is n % identical to the sequence of the variant polypeptide means that n % of the positions of the optimum global alignment between both sequences consists in identical amino acids.

The expression "immunogenic properties of a polypeptide" means that the polypeptide is capable of causing by itself or associated with an adjuvant of immunity or a carrier molecule if need be, an immune reaction, notably an immune response of the cellular type, for example a response of the CD4+ T cells.

For example, the variant polypeptide has a polypeptide sequence of less than 75 amino acids, preferably less than 60 amino acids.

As an illustration, the variant polypeptides may include conservative substitutions of amino acids in the sequence of the H2B histone of *Leishmania*, as illustrated above.

One or more amino acids of the reference polypeptide may be substituted, deleted or added, in order to form a variant polypeptide retaining at least 50% similarity, preferably at least 80% similarity, with the reference polypeptide, said variant polypeptide retaining the immunogenic properties of the reference polypeptide.

As opposed to the notion of identity, the notion of similarity concerns identical amino acids, and different amino acids but giving rise to a polypeptide which retains the immunogenic properties of the reference polypeptide; or only such different amino acids.

The fact that the sequence of the reference polypeptide is n % similar to the sequence of the variant polypeptide means that n % of the positions of the optimum global alignment between both sequences consist in identical amino acids and different amino acids, the presence of which in the polypeptide does not substantially change its immunogenic properties; or only such different amino acids.

In particular, substitutions in the polypeptides are conservative substitutions.

A conservative substitution is any substitution with a positive score in the Blosum62 substitution matrix, (Henikoff and Henikoff, 1992, Proc. Natl. Acad. Sci. USA 89: 10915-10919).

Another embodiment of polypeptide variants resorts to the preparation of peptides of the relevant H2B histone protein, said peptides having for example peptide sequences including 6 to 30, for example 6 to 20 or 6 to 15 amino acids, selected from the N-terminal sequence of the histone protein.

The peptides may be used as mixtures, including as mixotopes. Peptide mixtures for example comprise at least 2 or at least 5 peptide sequences different from each other or on the contrary having common consecutive amino acids.

The polypeptides (including the peptides) of the invention are prepared by any methods known to one skilled in the art, for example by chemical synthesis or by expression in a cellular, notably bacterial system, or in vitro in a "cell free" system.

The term "adjuvant" means any substance or compound capable of promoting or increasing the immune response against a determined active ingredient in a mammal, as compared with the immune response obtained under the same conditions by only administering the active ingredient alone.

In a specific exemplary embodiment of the invention, the adjuvant promotes an immune response of the cellular type. The adjuvant for example is CpG or any other authorized adjuvant in vaccinal use in humans or animals. The CpG concentration used for vaccinating mice is 1 µg/µl and the injected amount is 50 µg.

In a specific example, the immunogenic composition according to the invention, further comprises at least one other antigen of *Leishmania*, with immunogenic properties for triggering and/or promoting an immune response of the B and/or C type in a human or animal host.

The immunogenic composition according to the invention may further comprise at least one polypeptide consisting in a fragment of at least one additional histone protein of *Leishmania*.

Said fragment of a histone protein is notably selected from the H2A, H3 and H4 histone proteins. The histone protein is for example characteristic of *L. Major, L. Infantum, L. Donovani, L. Tropica, L. Enrietti*. Generally, the histone protein may be characteristic of a species selected in the whole of the *Leishmania* genus.

Said fragment may for example comprise all or part of the N-terminal region of said histone protein. Said fragment for example has a polypeptide sequence of less than 65 amino acids, preferably less than 50 amino acids.

In a specific example, the length of the sequence of said fragment accounts for 10 to 45% of the length of the histone protein.

The immunogenic composition according to the invention may alternatively comprise at least one entire histone protein of *Leishmania*, in association with the antigenic polypeptide of the H2B histone as described above.

Said at least one entire histone protein is notably selected from H2A, H3 and H4. It may be characteristic of *L. Major, L. Infantum, L. Donovani, L. Tropica, L. Enrietti*. Generally, said at least one entire histone protein may be characteristic of a species selected from the whole of the *Leishmania* genus.

Said immunogenic composition may be injected as such or with a pharmaceutically acceptable carrier. The immunogenic composition according to the invention may therefore further comprise a pharmaceutically acceptable carrier which may be administered to a human or animal host. A pharmaceutically acceptable carrier may easily be selected by one skilled in the art from water, polar substances such as ethylene glycol, polyethylene glycol, or propylene glycol, as well as from non-polar substances.

According to a particular embodiment of the invention, the immunogenic composition is capable of inducing a cellular type immune response of the effector T cells, for example CD4+ cells, when it is administered to a human of to an animal.

The T cells include effector cells of cell-mediation immunity (for example CD4+ or CD8+ T cells) as well as regulatory cells ("helper" and suppressive cells) of the immune responses. The polypeptide according to the invention preferentially activates effector cells of cell-mediation immunity.

In the present invention, the cellular type immune response may notably be an immune response of the Th1 type.

The polypeptide or the variant polypeptide is present, in the immunogenic composition according to the invention, in a concentration comprised between 0.01 µg/µl, and 5 µg/µl, for example between 0.01 µg/µl and 2 µg/µl, or between 0.4 µg/µl and 1 µg/µl.

The invention also deals with a polypeptide consisting in a fragment of the H2B histone protein of *Leishmania*, said fragment comprising all or part of the N-terminal region of said H2B histone protein.

In a specific example, the polypeptide is characteristic of the H2B histone of *Leishmania major*.

The polypeptide may be characteristic of the H2B histone protein of *L. Infantum, L. Donovani, L. Tropica, L. Enrietti*. Generally the polypeptide may be characteristic of a species selected from the whole of the *Leishmania* genus.

In a specific example, the polypeptide according to the invention has a polypeptide sequence of at least 65 amino acids, preferably less than 50 amino acids.

In a specific example, the polypeptide according to the invention has a polypeptide sequence of less than 65 amino acids, preferably less than 50 amino acids. The polypeptide has in this context a sequence comprising at least 6 consecutive amino acids of the N-terminal portion of the relevant H2B antigen.

The length of the sequence of said polypeptide for example accounts for 10 to 45% of the length of the histone protein.

Figure 1:
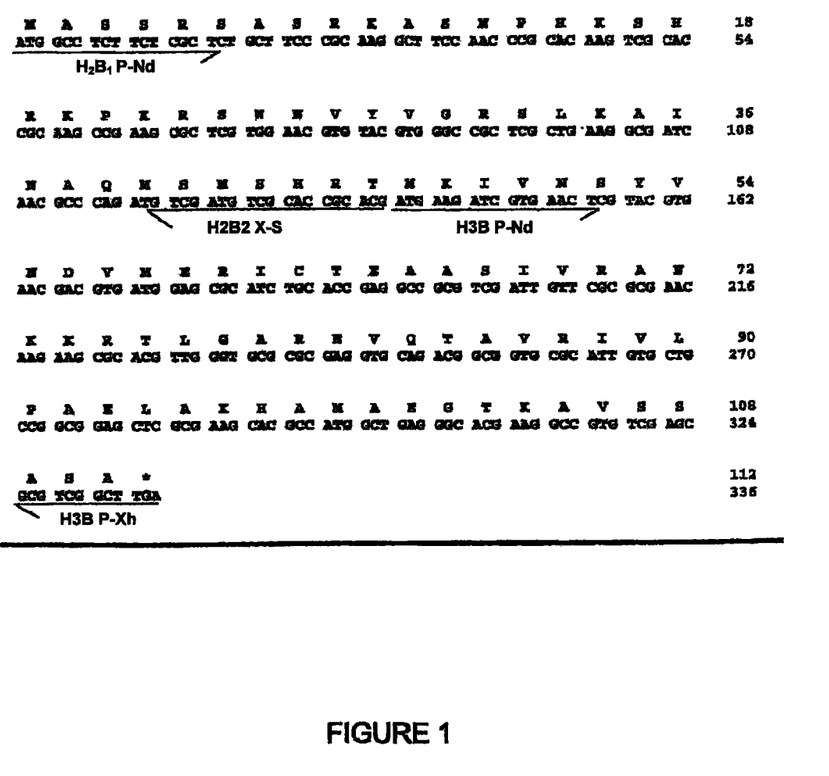
FIG. 1: The nucleotide (SEQ ID NO: 2) and protein sequence (SEQ ID NO: 1) of the H2B histone of *L. Major*. The sequences located by the notations H2B1 P-ND up, H2B2 X-S rev, H3B P-Nd up and H3B P-Xh rev correspond to the amplification primers of both portions, H2bΔC65(1-138 bp) (N-terminus) and H2bΔN46(139-333 bp) (C-terminus) of the protein.

In a specific example, the polypeptide according to the invention comprises the first 50 amino acids of the H2B histone protein, more particularly the first 46 amino acids of the H2B histone protein, as illustrated in FIG. 1.

The sequence of amino acids of a polypeptide according to the invention is for example the following: M A S S R S A S R K A S N P H K S H R K P K R S W N V Y V G R S L K A I N A Q M S M S H R T (residues 1-46 of SEQ ID NO: 1).

In a specific example, the polypeptide according to the invention is purified polypeptide or a polypeptide isolated from its production environment.

The object of the invention is also a variant polypeptide retaining at least 50% identity, preferably at least 80% identity with the polypeptide according to the invention. Said variant polypeptide has a substitution, a deletion or an addition of at least one amino acid, relatively to the sequence of said polypeptide and retains the immunogenic properties of said polypeptide.

The variant polypeptide has a polypeptide sequence of less than 75 amino acids, preferably less than 60 amino acids.

As an illustration, the variant polypeptides may include conservative substitutions of amino acids in the sequence of the H2B histone of *Leishmania*, as illustrated above.

Another embodiment of polypeptide variants resorts to the preparation of peptides from the relevant H2B histone protein, said peptides for example having peptide sequences including 6 to 30, for example 6 to 20 or 6 to 15 amino acids, selected from the N-terminal sequence of the histone protein.

The peptides may be used as mixtures, including as mixotopes. The peptide mixtures for example comprise at last 2 or at least 5 peptide sequences different from each other or on the contrary having common consecutive amino acids.

The polypeptides (including the peptides) of the invention are prepared by any method known to one skilled in the art, for example by chemical synthesis, or by expression in a cell notably bacterial system, or in vitro in a "cell free" system.

The invention also deals with a nucleic acid molecule coding for the polypeptide or variant polypeptide according to the invention.

The nucleotide sequence of said nucleic acid molecule may be the following or a portion of this sequence: ATG GCC TCT TCT CGC TCT GCT TCC CGC AAG GCT TCC AAC CCG CAC MG TCG CAC CGC MG CCG MG CGC TCG TGG MC GTG TAC GTG GGC CGC TCG CTG MG GCG ATC MC GCC CAG ATG TCG ATG TCG CAC CGC ACG (residues 1-138 of SEQ ID NO: 2).

The invention also concerns a vaccine with which protection may be obtained against infection by *Leishmania*.

The active ingredient of said vaccine comprises the polypeptide, the variant polypeptide or the nucleic acid molecule according to the invention. In a specific example, the vaccine further comprises an adjuvant stimulating the immune response when it is administered to a human or animal host, and generally said vaccine is prepared from an immunogenic composition according to the invention, as described above.

The term "vaccine" means an antigenic preparation with which prevention of microbial infections may be achieved by vaccination of a host. The vaccine according to the invention may alternatively be prepared for leading to a therapeutic activity against the infection.

The adjuvant for example promotes an immune response of the cellular type and in the case of the present invention this may be CpG.

Said vaccine may be administered, for example injected as such or with a pharmaceutically acceptable carrier. A pharmaceutically acceptable carrier may be easily selected by one skilled in the art from water, polar substances such as ethylene glycol, polyethylene glycol, or propylene glycol, as well as from non-polar substances.

In a specific example, the vaccine comprises at least another antigen of *Leishmania*, added as an active ingredient, said antigen having immunogenic properties for triggering and/or promoting an immune response of the B and/or T type in a human or animal host.

The vaccine may further comprise at least one polypeptide consisting in a fragment of at least one histone protein different from H2B of *Leishmania*, or a nucleic acid molecule coding for said polypeptide(s), or may further comprise at least one entire histone protein of *Leishmania*, in association with the antigenic polypeptide of the H2B histone described above, or a nucleic acid molecule coding for said entire histone protein(s).

Said fragment of a histone protein is notably selected from the H2A, H3 and H4 histone proteins. Generally, said at least one histone protein may be characteristic of a species selected from the whole of the *Leishmania* genus. Said at least one histone protein is for example characteristic of *L. Major, L. Infantum, L. Donovani, L. Tropica, L. Enrietti.*

Said fragment may for example comprise all or part of the N-terminal region of said histone protein. Said fragment for example has a polypeptide sequence of at least 65 amino acids, preferably less than 50 amino acids.

In a specific example, the length of the sequence of said fragment accounts for 10 to 45% of the length of the histone protein.

The vaccine according to the invention may be used for preventing or treating an infection by *Leishmania major*, when it is administered to a human or to an animal.

The vaccine according to the invention is capable of inducing a cellular type immune response of the effector T cells, for example the CD4+ cells when it is administered to a human or to an animal.

The T cells include effector cells of cell-mediation immunity (for example the CD4+ or CD8+ T cells) as well as regulatory cells ("helper" and suppressive cells) of the immune responses. The polypeptide according to the invention preferably activates effector cells of cell-mediation immunity.

This immune response of the cell type may notably be an immune response of the Th1 type.

It is known that CpG is capable of activating monocytes, macrophages, and dendritic cells. Thus, CpG injected at the same time as an antigen, may orient the immune response towards the Th1 type.

The administration routes of the vaccine according to the invention are diverse and comprise the intravenous, oral, transdermal and nasal routes; however the intramuscular and subcutaneous routes are the most current ones.

The active ingredient of the vaccine according to the invention is present in a sufficient amount. The expression "sufficient amount" means an amount or concentration of active ingredient capable of generating an immunity protection against Leishmaniases. If necessary, directives for the vaccination may prescribe repeated administration of vaccine doses.

The polypeptide or the variant polypeptide or the nucleic acid molecule is present in the vaccine according to the invention in a concentration between 0.01 µg/ml and 5 µg/µl, for example between 0.01 µg/µl and 2 µg/µl, or between 0.4 µg/µl and 1 µg/µl.

The invention finally concerns an expression vector capable of expressing the polypeptide or the variant polypeptide according to the invention, comprising a nucleic acid molecule according to the invention.

The term "expression vector" designates the means by which nucleic acids notably from DNA, from complementary DNA, from ARN or their variants, are introduced into a cell, particularly a prokaryotic cell, in order to express or produce a determined protein.

With the purpose of expressing a certain protein or a certain polypeptide, the expression vector may contain at least one promoter, at least one operator, at least one termination codon, as well as all the sequences required for effective transcription and translation of the nucleic acids from the vector. The whole of these elements is known to one skilled in the art.

The object of the invention is also host cells, for example prokaryotes, notably bacteria, transformed or transfected with an expression vector comprising a polynucleotide coding for the polypeptide according to the invention, under conditions allowing its expression.

The object of the invention is also a plasmid pET-CH2B containing the sequence of the carboxy-terminal portion of the H2B protein, deposited at the Collection Nationale de Cultures de Micro-organismes (CNCM) under No. I-3362, on Feb. 24, 2005.

The object of the invention is also a plasmid pET-NH2B containing the sequence of the divergent amino-terminal portion of the H2B protein, deposited at the Collection Nationale de Cultures de Micro-organismes (CNCM) under No. I-3363 on Feb. 24, 2005.

The object of the invention is also a plasmid pET-H2B containing the sequence of the H2B protein, deposited at the Collection Nationale de Cultures de Micro-organismes (CNCM) under No. I-3361 on Feb. 24, 2005.

CAPTIONS OF THE FIGURES

Well 1: raw extract of BL21 bacteria transformed by the respective recombinant plasmids and non-induced with IPTG.

Well 2: raw extract of BL21 bacteria transformed by the respective recombinant plasmids and induced with IPTG.

Well 3: recombinant histone proteins purified on a nickel column (H2B, H2BΔC65 and H2BΔN46 of *L. major*).

Well MW: molecular weight markers.

Well 1: raw extract of BL21 bacteria transformed by respective recombinant plasmids and non-induced with IPTG.

Wells 2, 3, 4: Recombinant histone proteins purified on a nickel column (H2B, H2BΔC65 and H2BΔN46 of *L. major*).

T+5 or 6: control group (PBS) after challenge with $10^5$ (5) or $10^6$ (6) parasites.

N+5 or 6: mice having received the amino-terminal region of H2B.

C+5 or 6: mice having received the carboxy-terminal region of H2B.

CpG+5 or 6: mice having only received the adjuvant (CpG).

The values represent the average of the lesions expressed in mm+/−standard deviation.

EXAMPLES

Equipment and Methods

Parasites and Culture Conditions

The parasite strain MHOM/TN/94/GLC94 (GLC94) isolated from a human lesion of zoonotic cutaneous leishmaniasis (LCZ) was used in the present work (Louzir et al., 1998). This isolate belongs to the *L. major* species, zymodeme MON25 (Kebaier et al., 2001). The parasites were grown on NNN medium at 26° C. and gradually transferred into RPMI (SIGMA, St Louis, Mo.) containing 2 mM L-glutamine, 100 U/ml penicillin, 100 µg/ml streptomycin and 10% inactivated fetal calf serum (complete medium). The promastigotes taken in the logarithmic growth phase, are adjusted to $10^6$ parasites/ml, in a constant volume of complete medium and then incubated at 26° C. The stationary growth phase is reached after 4-6 days of culture with densities of parasites ranging from $3.10^7$ to $8.10^7$ parasites/ml. The metacyclic promastigotes are then purified on a 5%-20% Ficoll gradient, washed, counted and then injected to the mice.

Figure 2:
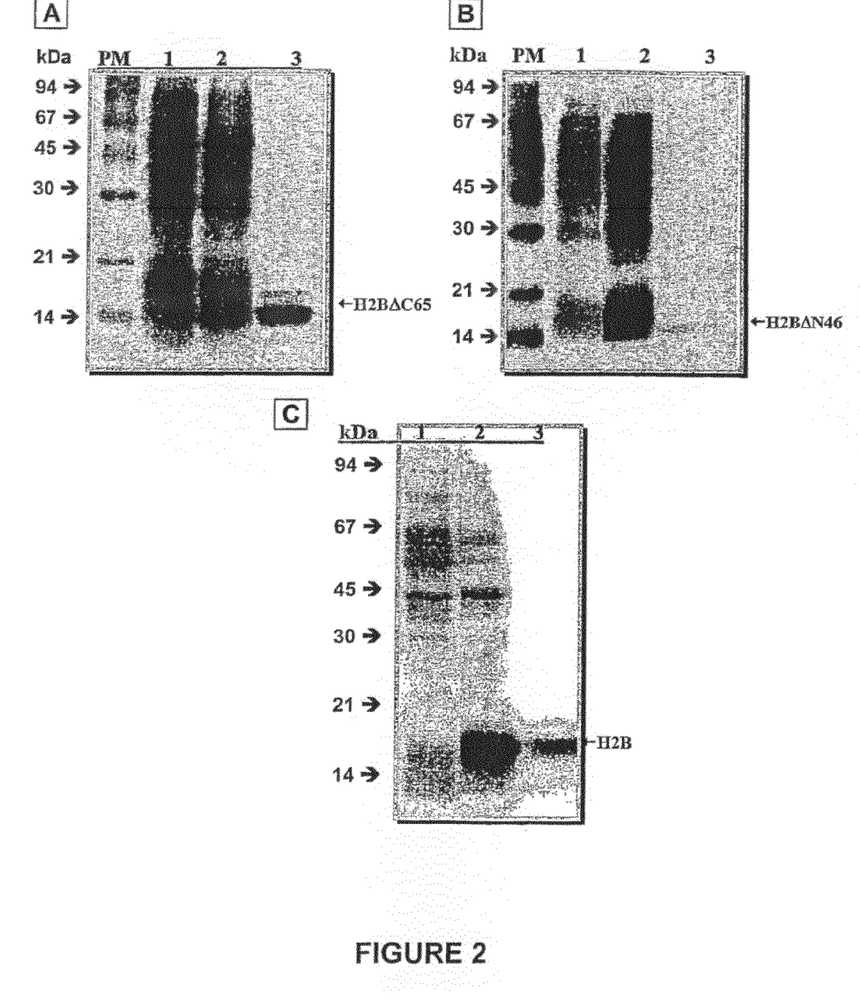
FIG. 2: Analysis of the expression and of the purification of recombinant histone proteins H2BΔC65(A), H2BΔN46(B, and H2B(C) of *L. Major* on 18% polyacrylamide gel after staining with Coomassie blue.

Expression and Purification of the Different Recombinant Proteins in *E. coli* BL21 Bacteria The sequences coding for the entire H2B histone protein (339 bp), the divergent amino-terminal portion (1-46aa) H2BΔC65 (138 bp) and the preserved carboxy-terminal portion (47-111aa) H2BΔN46 (198 bp) were cloned in the bacterial expression vector pET-22b (Novagen) (FIG. 1). The *E. coli* BL21 bacteria containing the recombinant plasmids (pET-22b-H2B, pET-H2BΔC65 and pET-H2BΔN46) were cultivated in LB medium and then the synthesis of the recombinant protein was induced in the presence of 1 mM isopropyl-1-thio-β-D-galactopyranoside (IPTG) for 4 hours. The recombinant proteins were purified by affinity chromatography on a nickel column ($Ni^{2+}$) (Amersham-Pharmacia). The purity of the produced proteins was checked with SDS-PAGE (FIG. 2).

The plasmid pET-CH2B containing the sequence of the carboxy-terminal portion of the H2B protein was deposited at the Collection Nationale de Cultures de Micro-organismes (CNCM) on Feb. 24, 2005 under No. I-3362.

Description of pET-CH2B: the plasmid pET-CH2B was obtained by cloning into the plasmid pET-22b+ (Novagen), the complementary DNA sequence coding for the H2B histone protein truncated by the first 46 amino acids (H2BΔN46) of *Leishmania major*. The H2BΔN46 gene was cloned at the restriction sites Ndel and Xhol of pET-22b+. *E. coli* XL1-blue recombinant bacteria were transformed with pET-CH2B. They are resistant to tetracyclin and ampicillin. The genes for resistance to tetracyclin and ampicillin are borne by the XL1-blue bacteria and the recombinant plasmid pET-22b+.

The pET-NH2B plasmid containing the sequence of the divergent amino-terminal portion of the H2B protein was deposited at the Collection Nationale de Cultures de Micro-organismes (CNCM), on Feb. 24, 2005, under No. I-3363.

Description of pET-NH2B: the plasmid pET-NH2B was obtained by cloning into the plasmid pET-22b+ (Novagen), the complementary DNA sequence coding for the H2B histone protein truncated by the last 65 amino acids (H2BΔC65) of Leishmania major.

The gene H2BΔC65 was cloned at the restriction sites NdeI and XhoI. E. coli XL1-blue recombinant bacteria were transformed with pET-NH2B. They are resistant to tetracyclin and ampicillin. The genes for resistance to tetracyclin and ampicillin are borne by the XL1-blue bacteria and the recombinant plasmid pET-22b+.

The pET-H2B plasmid containing the sequence of H2B protein was deposited at the Collection Nationale de Cultures de Micro-organismes (CNCM), on Feb. 24, 2005, under No. I-3361.

Description of pET-H2B: the plasmid pET-H2B was obtained by cloning into the plasmid pET-22b+ (Novagen), the complementary DNA sequence coding for the entire H2B histone protein of Leishmania major. The gene H2B was cloned at the restriction sites NdeI and XhoI.

E. coli XL1-blue recombinant bacteria were transformed with pET-H2B. They are resistant to tetracyclin and ampicillin. The genes for resistance to tetracyclin and ampicillin are borne by the XL1-blue bacteria and the recombinant plasmid pET-22b+.

The pET-H2B plasmid is further designated as pET-22b-H2B in the following.

The pET-CH2B plasmid is further designated as pET-H2BΔN46 in the following.

The pET-NH2B plasmid is further designated as pET-H2BΔC65 in the following.

The culture conditions for the transformed bacteria are the following:

Recommended Culture Medium

The recombinant bacteria are cultivated either in a liquid culture medium or in a solid culture medium.

The liquid culture medium, Luria Broth (LB) consists of: 1% (weight/volume) Bactotryptone, 0.5% (w/v) yeast extracts and 1% (w/v) NaCl. The pH of the medium should be adjusted to 7. This medium is recommended for multiplication of plasmids pET-22b+ containing the H2BΔC65 gene (or containing the H2BΔN46 gene or the H2B gene).

The solid culture medium, Luria Broth Agar (LB-Agar) consists of 1% (weight/volume) Bactotryptone, 0.5% (w/v) yeast extracts, 1% (w/v) NaCl and 1.5% (w/v) agar. This medium is essentially recommended when cultures are made from recombinant bacteria frozen to −80° C.

Both of these culture mediums are sterilized at 120° C. for 20 minutes just after their preparation.

Sowing Conditions

The recombinant bacteria frozen at −80° C. are first of all spread out on a dish containing LB-Agar solid culture medium supplemented with 15 μg/ml tetracyclin and 50 μg/ml ampicillin for 18 hours at 37° C. and then an isolated colony is picked up and incubated in 5 ml of LB added with the same antibiotics. Culture is performed for 18 hours at 37° C.

Incubation (Temperature, Atmosphere, Stirring, Illumination)

The culture temperature is always set to 37° C. with stirring at 200 rpm (SANYO Orbital Incubator device). Culture is performed under an ambient atmosphere and natural illumination.

Vaccination Procedure and Challenge of the Mice

Two experimental procedures were carried out; in the first protocol, the mice were injected twice at a 15 day interval with different vaccine preparations (Table 1). The second procedure was used for confirming and optimizing certain results (see details in Table 2).

All the injections were performed via a subcutaneous route, at the plantar cushion of the right hind paw in a final volume of 5 μl per injection. Four weeks after the last booster dose, the mice received an injection of L. major parasites (metacyclic promastigotes) at the plantar cushion of the right hind paw. Two amounts of parasites were used i.e. $10^5$ and $10^6$ parasites/injection. Tracking the course of the experimental disease was performed by weekly measurement of the diameter of the lesion.

TABLE 1

Experiment 1, experimental procedure for immunization and challenge of the mice.

| Group No. (numb. of mice) | Vaccinal preparations | Dosages | Injection route | Challenge |
|---|---|---|---|---|
| 1 (4 mice) | PBS | 50 μl | Subcutaneous | $10^5$ parasites |
| 2 (4 mice) | H2B + CpG | 25 μg/20 μg | Subcutaneous | $10^5$ parasites |
| 3 (4 mice) | H2B + nCpG | 25 μg/20 μg | Subcutaneous | $10^5$ parasites |
| 4 (4 mice) | H2BΔC65 + CpG | 25 μg/20 μg | Subcutaneous | $10^5$ parasites |
| 5 (4 mice) | H2BΔC65 + nCpG | 25 μg/20 μg | Subcutaneous | $10^5$ parasites |
| 6 (4 mice) | H2BΔN46 + CpG | 25 μg/20 μg | Subcutaneous | $10^5$ parasites |
| 7 (4 mice) | H2BΔN46 + nCpG | 25 μg/20 μg | Subcutaneous | $10^5$ parasites |
| 8 (4 mice) | CpG | 20 μg | Subcutaneous | $10^5$ parasites |
| 9 (4 mice) | nCpG | 20 μg | Subcutaneous | $10^5$ parasites |
| 10 (4 mice) | H2B | 25 μg | Subcutaneous | $10^5$ parasites |
| 11 (4 mice) | H2BΔC65 | 25 μg | Subcutaneous | $10^5$ parasites |
| 12 (4 mice) | H2BΔN46 | 25 μg | Subcutaneous | $10^5$ parasites |

TABLE 2

Experiment 2, experimental procedure for immunization and challenge of the mice.

| Group No. (numb. of mice) | Vaccinal preparations | Dosages/ volumes | Injection route | Challenge |
|---|---|---|---|---|
| 1 (6 mice) | CpG | 50 μg | Subcutaneous | $10^5$ parasites |
| 2 (6 mice) | CpG | 50 μg | Subcutaneous | $10^6$ parasites |
| 3 (6 mice) | H2BΔC65 + CpG | 20 μg/50 μg | Subcutaneous | $10^5$ parasites |
| 4 (6 mice) | H2BΔC65 + CpG | 20 μg/50 μg | Subcutaneous | $10^6$ parasites |
| 5 (6 mice) | H2BΔN46 + nCpG | 20 μg/50 μg | Subcutaneous | $10^5$ parasites |
| 6 (6 mice) | H2BΔN46 + CpG | 20 μg/50 μg | Subcutaneous | $10^6$ parasites |
| 7 (6 mice) | PBS | 50 μl | Subcutaneous | $10^5$ parasites |
| 8 (6 mice) | PBS | 50 μl | Subcutaneous | $10^6$ parasites |

Parasite Load

Quantitation of the parasites was estimated at the lesion sites by using a variant of the limiting dilution technique (Titus R G, Marchand M, Boon T, Louis J A. A limiting dilution assay for quantifying *Leishmania major* in tissues of infected mice. Parasite Immunol. 1985; 7:545-55). Briefly, the infected paw was cut, homogenized in a volume of 5 ml of RPMI medium added with antibiotics and then a series of dilutions from 1:10 to 1:10$^{11}$ was carried out in quadruplicate, each in a microtitration plate (96 wells, Nunc, Roskilde, Denmark) containing RPMI medium added with 100 U/ml penicillin, 100 µg/ml streptomycin, 2 mM L-glutamine and 10% decomplemented calf serum. The plates were incubated at 26° C. for at least 15 days. The search for living parasites is performed under an inverted microscope. The parasite load is expressed by the average of the negative log of the last dilution in which mobile parasites were detected.

Results

Production and Purification of Different Recombinant Proteins

Figure 3:
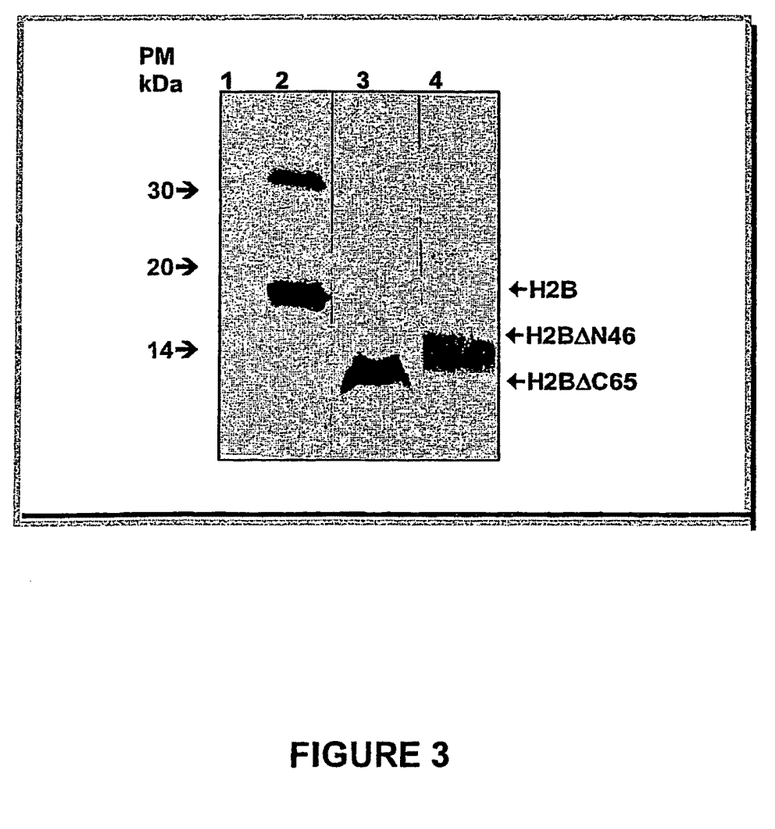
FIG. 3: Immunoblot analysis of the reactivity of rabbit anti-H2B polyclonal antibodies towards H2B, H2BΔC65 and H2BΔN46 recombinant histone proteins of *L. major* after purification on a nickel column.

The entire H2B protein (111aa), the divergent portion of H2B located at the first 46 aa and the preserved portion of H2B localized between amino acids 47 to 111 were first expressed by using the pET prokaryotic expression system and then purified by affinity chromatography on a nickel column (FIG. 2). The anti-H2B polyclonal antibody obtained after immunization of BALB/c mice by the entire H2B recombinant protein specifically recognizes by an immunoblot, the H2B, H2BΔC65 and H2BΔN46 recombinant proteins (FIG. 3).

Clinical and Parasitological Evaluation of the Effect of Vaccination of BALB/c Mice by the Entire or Mutated H2B Protein, Subsequent to Virulent Challenge by *L. major*

Preliminary experiments made on BALB/c mice vaccinated by the H2B protein alone or in the presence of an adjuvant (two injections of 20 mg of protein+/−25 µg of CpG at a 15 day interval) have shown that these mice were capable, one month after the last immunization, of producing large amounts of IFN-γ when the ganglion cells (draining the injection site) were re-stimulated in vitro with the H2B protein. The amounts of IL-10 or IL-4 are very small or undetectable. These results suggest that the H2B protein has the capacity of inducing a specific Th1 response in BALB/c mice.

The capacity of different vaccinal preparations of inducing protection in a murine model of experimental Leishmaniasis was evaluated in sensitive BALB/c mice by using two different and complementary experiments.

Experiment 1

BALB/c mice groups (4 mice per group), of 6 to 8 week old females, were injected twice at a 15 day interval with different vaccinal preparations (Table 1). The tested recombinant proteins were either adjuvated with CpG or with a negative control of CpG, non-CpG (nCpG). CpG is a non-methylated DNA oligodeoxynucleotide which has a particular CpG pattern. It has been clearly demonstrated in the literature that the CpG adjuvant is capable of activating monocytes, macrophages and denditric cells. Thus, CpG injected at the same time as an antigen may orientate the specific immune response towards the Th1 type (for a review, Klinman et al., 2004).

Two immunizations were therefore performed subcutaneously at the plantar cushion of the right hind paw. One month later, the different groups of BALB/c mice were infected with 2*10$^5$ metacyclic promastigotes of the virulent parasite strain of *L. major* (GLC94) at the plantar cushion of the left hind paw.

Figure 4:
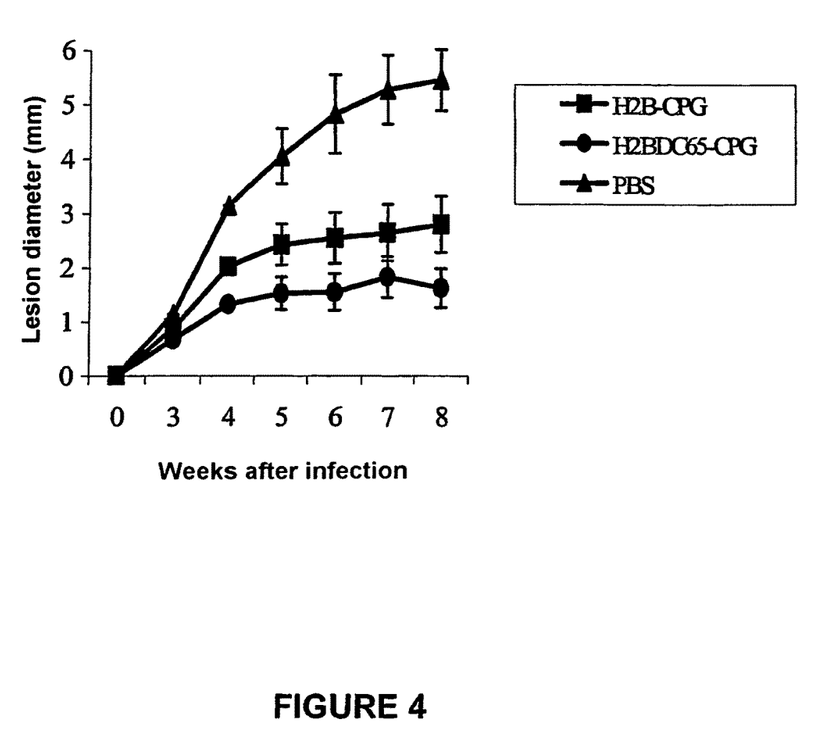
FIG. 4: Graphic illustration of the time change in diameter of the lesions in control BALB/c mice (PBS) or immunized by H2B (H2B-CpG) or just the amino-terminal portion of H2B (H2BDC65-CpG) in the presence of 25 µg of CpG/injection, used as an adjuvant. The mice were infected, 30 days after the booster dose, with $10^5$ promastigotes of *L. Major*. The values represent the average of the lesions expressed in mm+/−standard deviation.

The result of the change over time of the lesion in each batch of immunized and infected mice was expressed by the average of the size of the lesion obtained in mice of the same group. After an eight week clinical follow-up, only two batches of mice exhibited a very significant slowing down of the experimental lesions: these are the mice immunized by the entire H2B' protein in presence of CpG (H2B+CpG) and the mice immunized by the amino-terminal portion of H2B in presence of CpG (H2BΔC65+CpG). The differences were very significant with all the other groups, including the control mice group ($p<0.001$ from week 5) (FIG. 4). It is very interesting to point out that the mice immunized by the amino-terminal portion of H2B in the presence of CpG were more resistant than those immunized, under the same conditions, by the entire protein ($p<0.05$, from week 5) when they were then infected by *L. major*. Moreover, all the other groups developed an experimental disease similar to the one observed with the control mice (injected with PBS).

As a conclusion, the obtained results show that the NH2-terminal portion of the H2B protein and the entire H2B protein in the presence of the CpG adjuvant are capable of inducing a protective effect in BALB/c mice after virulent challenge by *L. major*. Further, comparison of the time course curves for the lesions between both of these batches of mice show better (statistically significative) resistance of the mice vaccinated with H2BΔC65+CpG as compared with mice vaccinated with H2B+CpG.

Evaluation of the Parasite Load

Figure 5:
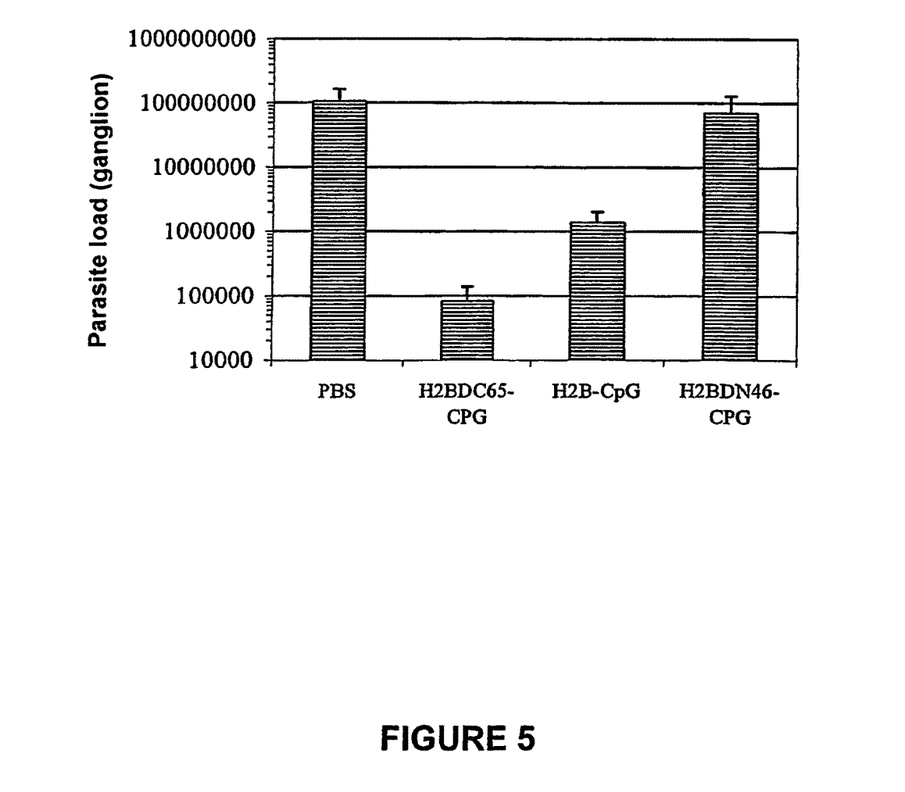
FIG. 5: Determination of the average of the number of parasites per ganglion by the limiting dilution technique in different batches of mice immunized twice subcutaneously, at the plantar cushion by H2B+CpG, H2BΔC65+CpG and H2BΔN46+CpG. Quantitation was achieved 8 weeks after the challenge by $10^6$ promastigotes of *L. major*. The results are expressed by the average of the number of parasites per ganglion from the strongest dilution in which at least one promastigote of *L. major* is viable.

Determination of the parasite load in the popliteal ganglion draining the lesion represents a determining factor in the evaluation of the anti-leishmanian vaccine (Kébaier et al.; 2001, "Heterogeneity of wild *Leishmania major* isolates in experimental murine pathogenicity and specific immune response, Infect. Immun. 2001, August, 69(8): 4906-15). The parasite load was only evaluated (8 weeks after experimental infection) in the mice groups below:

Control mice (PBS)
Mice vaccinated with H2B+CpG
Mice vaccinated with H2BΔC65+CpG
Mice vaccinated with H2BΔN46+CpG The results of the parasite load analyzed in the ganglion draining the injection site of the parasite are illustrated in FIG. 5. There is very good correlation between the parasite load and the severity of the experimental lesions induced in different groups of mice. The unprotected mice vaccinated with H2BΔN46 had a parasite load similar to the one found in control mice. On the other hand, both of the mice groups having received H2B or the amino-terminal portion (H2BΔC65) had a very clearly lower parasite load than that of the control groups (100 to 1,000 times less). It is interesting to point out that the mice immunized with the amino-terminal portion of H2B have an average parasite load at least 10 times lower than that found in mice immunized with the entire protein (H2B). These results confirm the superiority of the divergent (amino-terminal) portion as compared with the entire H2B protein, in its capacity of imparting protection to the sensitive BALB/c mice against a virulent challenge by *L. major*.

Experiment 2

With the purpose of confirming the results by notably using 10 times more parasites for the challenge, the inventors were interested in the truncated proteins of H2B (H2BΔC65 and H2BΔN46) by using a higher concentration of CpG (50 µg/injection) and three immunizations at 21 day intervals. Further, two control groups were used (one group having only received CpG and the other only the PBS buffer). One month after the last dose of vaccine, the mice were infected with two doses of parasite (i.e. 10$^5$ or 10$^6$ parasites (metacyclic promastigotes)/injection). The experimental procedure is detailed in Table 2.

Figure 6:
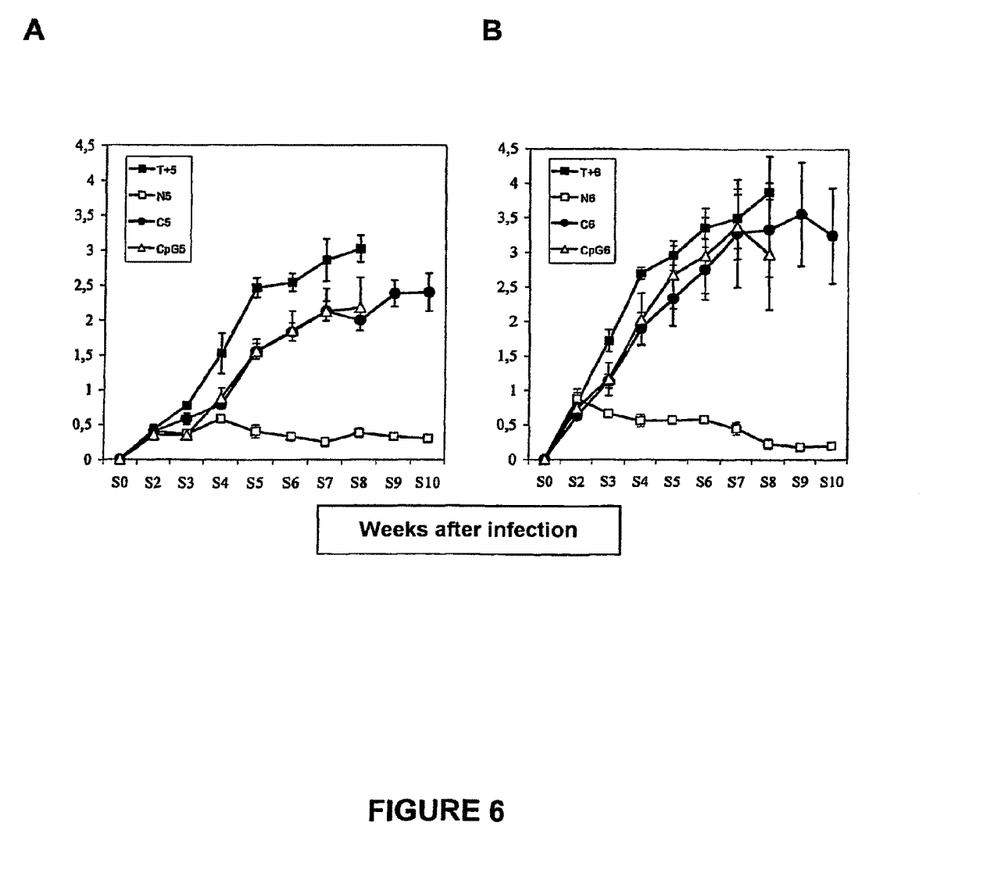
FIG. 6: Graphic illustration of the time change in the averages of the diameters of lesions (mm) in BALB/c mice, either vaccinated or not and after challenge by *L. major* in an amount of $10^5$ (A) or $10^6$ (B) metacyclic promastigotes.
Figure 7:
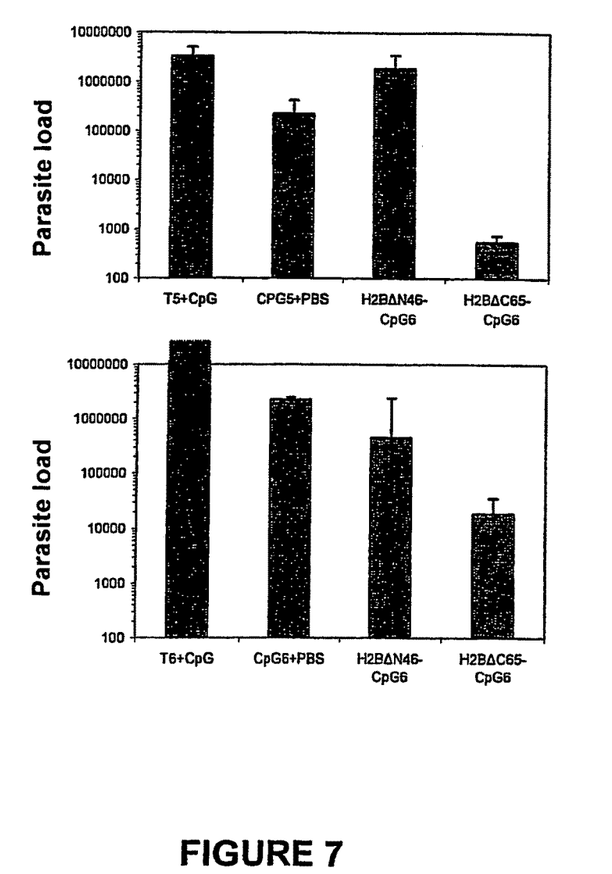
FIG. 7: Determination of the parasitic load by the limiting dilution technique in different batches of mice immunized thrice sub-cutaneously, at the plantar cushion by H2BΔN46+CpG, H2BΔC65+CpG as well as by the CpG controls. Quantitation was achieved 10 weeks after challenge by $10^5$ or $10^6$ promastigotes of *L. Major*. The results are expressed as in FIG. 5.

FIGS. 6 and 7 clearly show that only the mice immunized with the divergent portion of the H2B protein (H2BΔC65)

were resistant to experimental infection by *L. major* even after using 10⁶ metacyclic promastigotes for the challenge. There is perfect correlation between the clinical resistance and the parasite load achieved at the end of the procedure (10 weeks after infection).

These results confirm those obtained with the first experiment and suggest that the second immunization procedure imparts better protection to the BALB/c mice against infection by *L. major*.

Discussion

According to figures from the World Health Organization (WHO), leishmaniases in 88 countries threaten 350 million people exposed to the risk of stings of phlebotoma, vector insects, and the number of affected individuals is estimated to be 12 million. In its most severe form, this disease kills. The fact that the majority of the individuals having developed leishmaniases, or just simply an asymptomatic infection, resist re-infection, justifies the research work for developing vaccines. However, two major problems remain posed: better knowledge of the exact nature of the effector mechanisms of resistance as well as of the nature of the parasite antigens and the adjuvant to be used. Presently there is no vaccine for human use. The first generation vaccines, the only ones which have been tested in humans, have shown their ineffectiveness (Sharifi et al., 1998; Khalil et al., 2000; De Luca et al., 2001; Armijos et al., 2004).

The experiments reported here allow identification and evaluation of new vaccine candidates against Leishmaniases.

The *L. infantum* H2B histone protein was initially selected in the laboratory as a parasite protein of low molecular weight capable of inducing a Th1 response in humans. More recent data have suggested the role of this protein as a vaccine candidate (Melby, 2000; Probst et al. 2001; Iborra et al., 2004).

The studies described here are based on compared analysis of immunogenicity and of the protective role of two (divergent and preserved) regions of the H2B recombinant protein of *Leishmania* as well as of the entire protein. The results clearly show that the amino-terminal (divergent) portion of H2B adjuvated with CpG has imparted very good protection to BALB/c sensitive mice against virulent challenge by *L. major*. Conversely, the preserved (carboxy-terminal) portion, injected under the same conditions did not have any protective effect. It is extremely interesting to point out that the entire H2B protein imparted intermediate protection. The whole of the results suggests that the amino-terminal (divergent) portion of H2B may be a good vaccine candidate against leishmaniases.

REFERENCES

Alimohammadian M H, Khamesipour A, Darabi H, et al. The role of BCG in human immune responses induced by multiple injections of autoclaved *Leishmania major* as a candidate vaccine against leishmaniasis. Vaccine 2002; 21:174-80.

Armijos R X, Weigel M M, Calvopina M, Hidalgo A, Cevallos W, Correa J. Safety, immunogenicity, and efficacy of an autoclaved *Leishmania amazonensis* vaccine plus BCG adjuvant against New World cutaneous leishmaniasis. Vaccine, 2004, Mar. 12; 22(9-10):1320-6.

Belkaid Y, Piccirillo C A, Mendez S, Shevach E M, Sacks D L: CD4+CD25+ regulatory T cells control *Leishmania major* persistence and immunity. Nature 2002; 420:502-507.

Brodskyn C, Beverley S M, Titus R G. Virulent or avirulent (dhfr-ts−) *Leishmania major* elicit predominantly a type-1 cytokine response by human cells in vitro. Clin. Exp. Immunol. 2000; 119(2):299-304.

Campbell K, Diao H, Ji J, Soong L. DNA immunization with the gene encoding P4 nuclease of *Leishmania amazonensis* protects mice against cutaneous Leishmaniasis. Infect. Immun. 2003; 71(11):6270-8.

Campos-Neto A, Webb J R, Greeson K, Coler R N, Skeiky Y A, Reed S G. Vaccination with plasmid DNA encoding TSA/LmSTl1 leishmanial fusion proteins confers protection against *Leishmania major* infection in susceptible BALB/c mice. Infect. Immun. 2002; 70(6):2828-36.

Coler R N, Skeiky Y A, Bernards K, Greeson K, Carter D, Cornellison C D, Modabber F, Campos-Neto A, Reed S G. Immunization with a polyprotein vaccine consisting of the T-Cell antigens thiol-specific antioxidant, *Leishmania major* stress-inducible protein 1, and *Leishmania* elongation initiation factor protects against leishmaniasis. Infect. Immun. 2002; 70(8):4215-25.

Davies C R, Lianos-Cuentas E A, Pyke S D M et al. Cutaneous leishmaniasis in the Peruvian Andes: an epidemiological study of infection and immunity. Epidemiol. Infect. 1995; 114: 297-318.

De Luca P M, Mayrink W, Pinto J A, et al. A randomized double-blind placebo-controlled trial to evaluate the immunogenicity of a candidate vaccine against American tegumentary leishmaniasis. Acta Trop. 2001; 80:251-60.

Desjeux P. Leishmaniasis. Public health aspects and control. Clin. Dermatol. 1996; 14:417-23.

Dumonteil E, Maria Jesus R S, Javier E O, Maria del Rosario G M. DNA vaccines induce partial protection against *Leishmania mexicana*. Vaccine. 2003; 21(17-18):2161-8.

Gavin, M. and Rudensky, A. Control of immune homeostasis by naturally arising regulatory CD4+ T cells. Curr. Opin. Immunol. 2003; 15(6):690-6.

Guirges S Y. Natural and experimental re-infection of man with oriental score. Ann. Trop. Med. Parasitol. 1971; 65:197-205.

Gurunathan S, Sacks D L, Brown D R, Reiner S L; Charest H, Glaichenhaus N, Seder R A. Vaccination with DNA encoding the immunodominant LACK parasite antigen confers protective immunity to mice infected with *Leishmania major*. J. Exp. Med. 1997; 186(7):1137-47.

Handman E, Symons F M, Baldwin T M, Curtis J M, Scheerlinck J P. Protective vaccination with promastigote surface antigen 2 from *Leishmania major* is mediated by a TH1 type of immune response. Infect. Immun. 1995; 63(11): 4261-7.

Iborra S, Soto M, Carrion J, Nieto A, Fernandez E, Alonso C, Requena J M. The *Leishmania infantum* acidic ribosomal protein P0 administered as a DNA vaccine confers protective immunity to *Leishmania major* infection in BALB/c mice. Infect. Immun. 2003; 71(11):6562-72.

Iborra S, Soto M, Carrion J, Alonso C, Requena J M. Vaccination with a plasmid DNA cocktail encoding the nucleosomal histones of *Leishmania* confers protection against murine cutaneous leishmaniasis. Vaccine. 2004; 22 (29-30):3865-76.

Kébaier C, Louzir H, Chemk M, Ben Salah A, Dellagi K. Heterogeneity of wild *Leishmania major* isolates in experimental murine pathogenicity and specific immune response. Infection and Immunity. 2001. 69(8), 4906-4915.

Khalil, E A, El Hassan A M, Zijlstra E E, et al. Autoclaved *Leishmania major* vaccine for prevention of visceral leishmaniasis: a randomised, double-blind, BCG-controlled trial in Sudan. Lancet 2000; 356:1565-9.

Klinman D M. Use of CpG oligodeoxynucleotides as immunoprotective agents. Expert Opin. Biol. Ther. 2004; 4(6): 937-46.

WHO Expert Committee. Control of the Leishmaniasis. WHO Tech. Rep. Ser. 1990; 793: 0-158.

Louzir H, Melby P C, Ben Salah A, Marrakchi H, Aoun K, Ben Ismail R, Dellagi K. Immunologic determinants of disease evolution in localized cutaneous leishmaniasis due to Leishmania major. Journal of Infectious Diseases. 1998. 177(6), 1687-1695.

Maalej I A, Chemk M, Louzir H, Ben Salah A, Bahloul C, Amri F, Dellagi K. Comparative evaluation of ELISAs based on ten recombinant or purified Leishmania antigens for the serodiagnosis of Mediterranean visceral leishmaniasis. Am. J. Trop. Med. Hyg. 2003; 68(3):312-20.

Melby P C, Ogden G B, Flores H A, Zhao W, Geldmacher C, Biediger N M, Ahuja S K, Uranga J, Melendez M. Identification of vaccine candidates for experimental visceral leishmaniasis by immunization with sequential fractions of a cDNA expression library. Infect. Immun. 2000; 68(10):5595-602.

Probst P, Stromberg E, Ghalib H W, Mozel M, Badaro R, Reed S G, Webb J R. Identification and characterization of T cell-stimulating antigens from Leishmania by CD4 T cell expression cloning. J. Immunol. 2001; 166(1):498-505.

Ramiro M J, Zarate J J, Hanke T, Rodriguez D, Rodriguez J R, Esteban M, Lucientes J, Castillo J A, Larraga V. Protection in dogs against visceral leishmaniasis caused by Leishmania infantum is achieved by immunization with a heterologous prime-boost regime using DNA and vaccinia recombinant vectors expressing LACK. Vaccine. 2003; 21(19-20):2474-84.

Sharifi I, Reza A, Aflatonian M R, et al. Randomised vaccine trial of single dose of killed Leishmania major plus BCG against anthroponotic cutaneous leishmaniasis in Bam, Iran. Lancet 1998; 351:1540-3.

Skeiky Y A, Coler R N, Brannon M, Stromberg E, Greeson K, Crane R T, Webb J R, Campos-Veto A, Reed S G. Protective efficacy of a tandemly linked, multi-subunit recombinant leishmanial vaccine (Leish-111f) formulated in MPL adjuvant. Vaccine. 2002; 10; 20 (27-28):3292-303.

Skeiky Y A, Kennedy M, Kaufman D, Borges M M, Guderian J A, Scholler J K, Ovendale P J, Picha K S, Morrissey P J, Grabstein K H, Campos-Neto A, Reed S G. LeIF: a recombinant Leishmania protein that induces an IL-12-mediated Th1 cytokine profile. J. Immunol. 1998; 161(11):6171-9.

Soto M, Requena J M, Quijada L, Perez M J, Nieto C G, Guzman F, Patarroyo M E, Alonso C. Antigenicity of the Leishmania infantum histones H2B and H4 during canine viscerocutaneous leishmaniasis. Clin. Exp. Immunol. 1999; 115(2):342-9.

Spitzer N, Jardim A, Lippert D, Olafson R W. Long-term protection of mice against Leishmania major with a synthetic peptide vaccine. Vaccine. 1999 Mar. 17; 17 (11-12): 1298-300.

Streit J A, Recker T J, Filho F G, Beverley S M, Wilson M E. Protective immunity against the protozoan Leishmania chagasi is induced by subclinical cutaneous infection with virulent but not avirulent organisms. J. Immunol. 2001; 166(3):1921-9.

Wolffe A P. Transcriptional regulation in the context of chromatin structure. Essays Biochem. 2001; 37:45-57.

---

The invention claimed is:

1. An immunogenic composition consisting essentially of:
(1) an antigenic polypeptide consisting of a fragment of the H2B histone protein of *Leishmania major*, wherein the fragment consists of no more than 75 consecutive amino acid residues of SEQ ID NO: 1 with the proviso that the fragment includes residues 1-46 of SEQ ID NO: 1; and
(2) an immune response stimulating amount of an adjuvant.

2. The immunogenic composition according to claim 1, wherein the polypeptide consists of less than 65 amino acids.

3. The immunogenic composition according to claim 1, wherein one or more amino acids of the polypeptide is substituted with a different amino acid, wherein the substitution is a conservative substitution.

4. The immunogenic composition according to claim 3, wherein the polypeptide consists of less than 60 amino acids.

5. The immunogenic composition according to claim 1, in which the adjuvant promotes a cellular immune response.

6. The immunogenic composition according to claim 1, wherein the adjuvant is CpG.

7. The immunogenic composition according to claim 1, further comprising at least one other antigen of *Leishmania* having immunogenic properties for triggering and/or promoting an immune response of type B and/or T in an human host or animal.

8. The immunogenic composition according to claim 1, further comprising at least one polypeptide consisting of a fragment of at least one additional histone protein of *Leishmania*.

9. The immunogenic composition according to claim 1, further comprising histone protein of *Leishmania*.

10. The immunogenic composition according to claim 8, wherein said at least one additional histone protein is selected from H2A, H3, and H4.

11. The immunogenic composition according to claim 8, wherein said *Leishmania* is *L. major, L. Infantum, L. Donovani, L. Tropica,* or *L. Enrietti*.

12. The immunogenic composition according to claim 1, comprising at least one pharmaceutically acceptable carrier for administration to a human or animal host.

13. The immunogenic composition according to claim 1, which induces an effector T cell immune response when it is administered to a human or an animal.

14. The immunogenic composition according to claim 13, which induces a Th1 immune response.

15. The immunogenic composition according to claim 1, wherein the polypeptide is present in an amount between 0.01 µg/µl and 5 µg/µl.

16. An antigenic polypeptide consisting of a fragment of the H2B histone protein of *Leishmania major*, wherein the fragment consists of no more than 75 consecutive amino acid residues of SEQ ID NO: 1, the proviso that the fragment includes residues 1-46 of SEQ ID NO: 1.

17. The antigenic polypeptide according to claim 16 consisting of less than 65 amino acids.

18. The antigenic polypeptide according to claim 16, wherein one or more amino acids of the polypeptide is substituted with a different amino acid, wherein the substitution is a conservative substitution.

19. The antigenic polypeptide according to claim 18, wherein the polypeptide consists of less than 60 amino acids.

20. The antigenic polypeptide according to claim 16, which induces an effector T cell immune response when it is administered to a human or an animal.

21. The antigenic polypeptide according to claim 20, which induces a Th1 immune response.

* * * * *

UNITED STATES PATENT AND TRADEMARK OFFICE
CERTIFICATE OF CORRECTION

PATENT NO.       : 8,551,500 B2                                     Page 1 of 1
APPLICATION NO.  : 12/149841
DATED            : October 8, 2013
INVENTOR(S)      : Mehdi Chenik et al.

It is certified that error appears in the above-identified patent and that said Letters Patent is hereby corrected as shown below:

IN THE CLAIMS:

Claim 16, col. 20, line 48, "the proviso" should read --with the proviso--.

Signed and Sealed this
Seventeenth Day of December, 2013

Margaret A. Focarino
*Commissioner for Patents of the United States Patent and Trademark Office*

SEQUENCE LISTING

```
<160> NUMBER OF SEQ ID NOS: 2

<210> SEQ ID NO 1
<211> LENGTH: 111
<212> TYPE: PRT
<213> ORGANISM: Leishmania major

<400> SEQUENCE: 1

Met Ala Ser Ser Arg Ser Ala Ser Arg Lys Ala Ser Asn Pro His Lys
1               5                   10                  15

Ser His Arg Lys Pro Lys Arg Ser Trp Asn Val Tyr Val Gly Arg Ser
            20                  25                  30

Leu Lys Ala Ile Asn Ala Gln Met Ser Met Ser His Arg Thr Met Lys
        35                  40                  45

Ile Val Asn Ser Tyr Val Asn Asp Val Met Glu Arg Ile Cys Thr Glu
    50                  55                  60

Ala Ala Ser Ile Val Arg Ala Asn Lys Lys Arg Thr Leu Gly Ala Arg
65                  70                  75                  80

Glu Val Gln Thr Ala Val Arg Ile Val Leu Pro Ala Glu Leu Ala Lys
                85                  90                  95

His Ala Met Ala Glu Gly Thr Lys Ala Val Ser Ser Ala Ser Ala
            100                 105                 110

<210> SEQ ID NO 2
<211> LENGTH: 336
<212> TYPE: DNA
<213> ORGANISM: Leishmania major
<220> FEATURE:
<221> NAME/KEY: CDS
```

```
<222> LOCATION: (1)..(333)

<400> SEQUENCE: 2 atg gcc tct tct cgc tct gct tcc cgc aag gct tcc aac ccg cac aag        48
Met Ala Ser Ser Arg Ser Ala Ser Arg Lys Ala Ser Asn Pro His Lys
1               5                   10                  15 tcg cac cgc aag ccg aag cgc tcg tgg aac gtg tac gtg ggc cgc tcg        96
Ser His Arg Lys Pro Lys Arg Ser Trp Asn Val Tyr Val Gly Arg Ser
                20                  25                  30 ctg aag gcg atc aac gcc cag atg tcg atg tcg cac cgc acg atg aag       144
Leu Lys Ala Ile Asn Ala Gln Met Ser Met Ser His Arg Thr Met Lys
            35                  40                  45 atc gtg aac tcg tac gtg aac gac gtg atg gag cgc atc tgc acc gag       192
Ile Val Asn Ser Tyr Val Asn Asp Val Met Glu Arg Ile Cys Thr Glu
        50                  55                  60 gcc gcg tcg att gtt cgc gcg aac aag aag cgc acg ttg ggt gcg cgc       240
Ala Ala Ser Ile Val Arg Ala Asn Lys Lys Arg Thr Leu Gly Ala Arg
65                  70                  75                  80 gag gtg cag acg gcg gtg cgc att gtg ctg ccg gcg gag ctc gcg aag       288
Glu Val Gln Thr Ala Val Arg Ile Val Leu Pro Ala Glu Leu Ala Lys
                85                  90                  95 cac gcc atg gct gag ggc acg aag gcc gtg tcg agc gcg tcg gct tga       336
His Ala Met Ala Glu Gly Thr Lys Ala Val Ser Ser Ala Ser Ala
                100                 105                 110
```